（12）United States Patent
Lindenthaler

(10) Patent No.: US 8,731,683 B2
(45) Date of Patent: May 20, 2014

(54) STIMULATION SYSTEM AND METHOD FOR VOICE LIFT

(71) Applicant: MED-EL Elektromedizinische Geraete GmbH, Innsbruck (AT)

(72) Inventor: Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/708,146

(22) Filed: Dec. 7, 2012

(65) Prior Publication Data
US 2013/0150926 A1 Jun. 13, 2013

Related U.S. Application Data

(60) Provisional application No. 61/567,664, filed on Dec. 7, 2011, provisional application No. 61/567,666, filed on Dec. 7, 2011.

(51) Int. Cl.
*A61N 1/00* (2006.01)
(52) U.S. Cl.
USPC .......................................................... 607/62
(58) Field of Classification Search
USPC ................... 607/62, 42, 48, 72; 600/587
See application file for complete search history.

(56) References Cited

U.S. PATENT DOCUMENTS

| | | | | |
|---|---|---|---|---|
| 5,016,647 | A | * | 5/1991 | Sanders .......................... 607/72 |
| 5,111,814 | A | * | 5/1992 | Goldfarb ......................... 607/48 |
| 2002/0156507 | A1 | | 10/2002 | Lindenthaler |
| 2007/0123950 | A1 | | 5/2007 | Ludlow et al. |
| 2009/0187124 | A1 | | 7/2009 | Ludlow et al. |
| 2009/0270943 | A1 | | 10/2009 | Maschino |
| 2011/0125212 | A1 | * | 5/2011 | Tyler .............................. 607/42 |
| 2013/0053926 | A1 | * | 2/2013 | Hincapie Ordonez et al. . 607/62 |
| 2013/0131551 | A1 | * | 5/2013 | Raghunathan et al. ........ 600/587 |

OTHER PUBLICATIONS

International Searching Authority, International Search Report and the Written Opinion for International Application No. PCT/US2012/068567, 15 pages, Feb. 8, 2013.

\* cited by examiner

*Primary Examiner* — Robert N Wieland
(74) *Attorney, Agent, or Firm* — Sunstein Kann Murphy & Timbers LLP

(57) ABSTRACT

A stimulation system and method for providing training therapy to a human subject having a weakened voice includes an activating switch configured to generate a first signal, and a processor configured to receive the first signal from the sensing electrode and to generate at least one stimulation parameter based on the first signal. The system further includes a stimulating electrode configured to receive the stimulation parameter from the processor and to activate a recurrent laryngeal nerve or vagus nerve of the subject in response to the stimulation parameter.

21 Claims, 5 Drawing Sheets

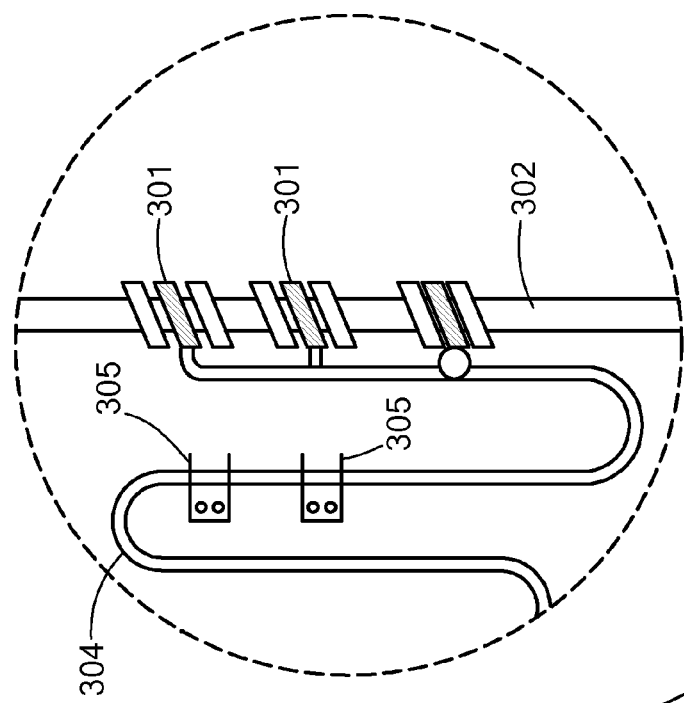
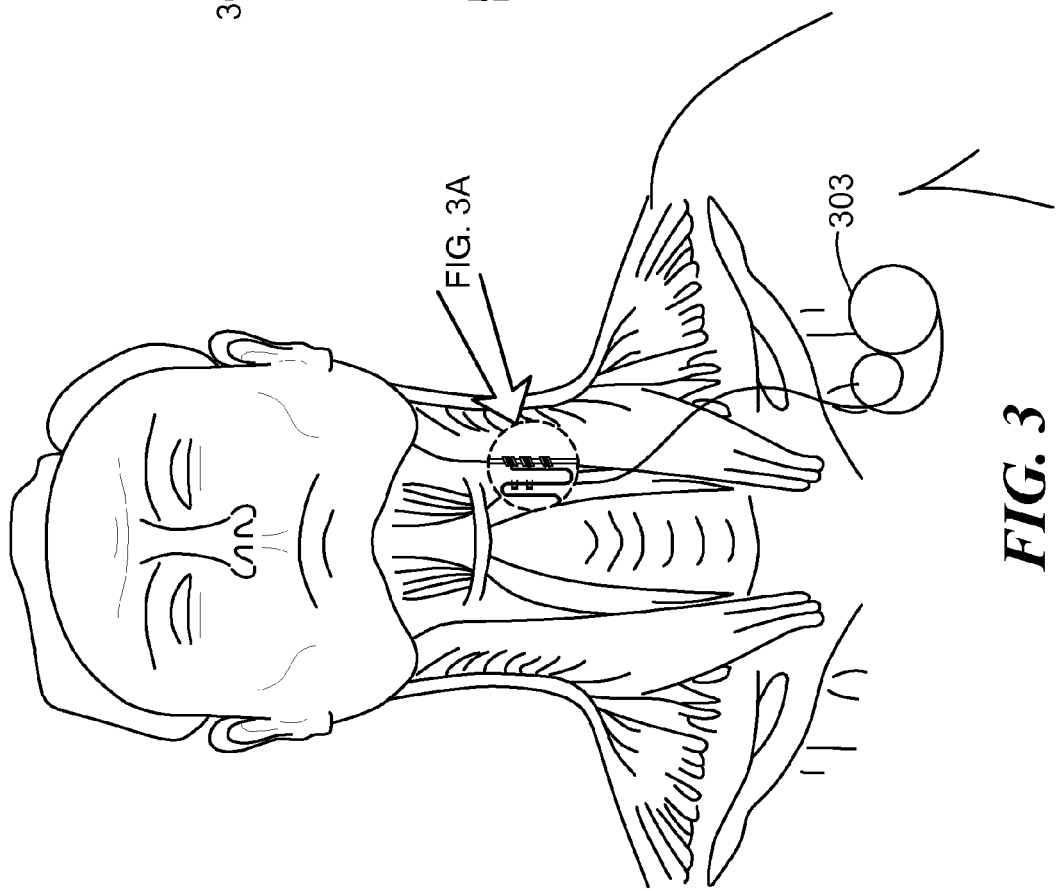
FIG. 3A
FIG. 3

STIMULATION SYSTEM AND METHOD FOR VOICE LIFT

CROSS REFERENCE TO RELATED APPLICATIONS

The present application claims priority to U.S. Provisional Patent Application No. 61/567,664 filed Dec. 7, 2011 and U.S. Provisional Patent Application No. 61/567,666 filed Dec. 7, 2011, the disclosures of which are incorporated by reference herein in their entirety.

The present application is also related to U.S. patent application Ser. No. 13/708,129 filed on Dec. 7, 2012 and published as U.S. Patent Application Publication No. 2013/0150924, and U.S. patent application Ser. No. 13/708,111 filed on Dec. 7, 2012 and published as U.S. Patent Application Publication No. 2013/0150908, the disclosures of which are incorporated by reference herein in their entirety.

TECHNICAL FIELD

The present invention relates to a training therapy for voice lift, and in particular, to devices and methods for stimulating the recurrent laryngeal nerve (RLN) or the glottic closure reflex of a human subject to treat a weak voice.

BACKGROUND ART

Voicing occurs when air is expelled from the lungs through the glottis, creating a pressure drop across the larynx. When this drop becomes sufficiently large, the vocal folds start to oscillate. The minimum pressure drop required to achieve phonation is called the phonation threshold pressure, and for humans with normal vocal folds, it is approximately 2-3 cm $H_2O$. The motion of the vocal folds during oscillation is mostly laterally, though there is also some superior component as well. However, there is almost no motion along the length of the vocal folds. The oscillation of the vocal folds serves to modulate the pressure and flow of the air through the larynx, and this modulated airflow is the main component of the sound of most voiced phones.

The vocal folds will not oscillate if they are not sufficiently close to one another, are not under sufficient tension or under too much tension, or if the pressure drop across the larynx is not sufficiently large. In linguistics, a phone is called voiceless if there is no phonation during its occurrence. In speech, voiceless phones are associated with vocal folds that are elongated, highly tensed, and placed laterally (abducted) when compared to vocal folds during phonation.

Fundamental frequency, the main acoustic cue for the percept pitch, can be varied through a variety of means. Large scale changes are accomplished by increasing the tension in the vocal folds through contraction of the cricothyroid muscle. Smaller changes in tension can be effected by contraction of the thyroarytenoid muscle or changes in the relative position of the thyroid and cricoid cartilages, as may occur when the larynx is lowered or raised, either volitionally or through movement of the tongue to which the larynx is attached via the hyoid bone. In addition to tension changes, fundamental frequency is also affected by the pressure drop across the larynx, which is mostly affected by the pressure in the lungs, and will also vary with the distance between the vocal folds. Variation in fundamental frequency is used linguistically to produce intonation and tone.

The voicing mechanism that is specifically designed for voice production is the larynx. The larynx is between the pharynx and the trachea. It communicates with the mouth and the nose though the laryngeal and oral parts of the pharynx. Although the larynx is part of the air passages, the larynx normally acts as a valve for preventing swallowed food and foreign bodies from entering the lower respiratory passages. The larynx is located in the anterior portion of the neck.

The laryngeal skeleton comprises nine cartilages that are joined by various ligaments and membranes. Three of the cartilages are single (thyroid, cricoid and epiglottis), and three are paired (arytenoid, corniculate, and cuneiform).

The extrinsic muscles of the larynx move the larynx as a whole. The infrahyoid muscles (omohyoid, sternohyoid, and sternothyroid) are depressors of the hyoid bone and the larynx, whereas the suprahyoid muscles (stylohyoid, digastric, mylohyoid and geniohyoid) and the stylopharyngeus are elevators of the hyoid bone and larynx.

The intrinsic muscles of the larynx are concerned with the movements of the laryngeal parts, making alterations in the length and tension of the vocal folds and in the size and shape of the rima glottidis in voice production. All intrinsic muscles of the larynx are supplied by the recurrent laryngeal nerve (RLN), a branch of the vagus nerve (CN X) except the cricothyroid muscle, which is supplied by the external laryngeal nerve.

The adductors of the vocal folds include the lateral cricoarytenoid muscles which arise from the lateral portions of the cricoid cartilage and insert into the muscular processes or the arytenoid cartilages. These muscles pull the muscular processes anteriorly, rotating the arytenoid cartilages so that their vocal processes swing medially. These movements adduct the vocal folds and close the rima glottidis.

The principle abductors of the vocal folds are the posterior cricoarytenoid muscles. These muscles arise on each side from the posterior surface of the lamina of the cricoid cartilage and pass laterally and superiorly to insert into the muscular processes of the arytenoid cartilages. They rotate the arytenoid cartilages, thereby deviating them laterally and widening the rima glottidis.

The main tensors of the vocal folds are the triangular cricothyroid muscles. These are located on the external surface of the larynx between the cricoid and thyroid cartilages. The muscle on each side arises from the anterolateral part of the cricoid cartilage and inserts into the inferior margin and anterior aspect of the inferior horn of the thyroid cartilage. These muscles tilt the thyroid cartilage anteriorly on the cricoid cartilage, increasing the distance between the thyroid and arytenoid cartilages. As a result, the vocal ligaments are elongated and tightened and the pitch of the voice is raised.

The principle relaxers of the vocal folds are the broad thyroarytenoid muscles. They arise from the posterior surface of the thyroid cartilage near the median plane and insert into the anterolateral surfaces of the arytenoid cartilages. One band of its inferior deep fibers, called the vocalis muscle, arises from the vocal ligament and passes to the vocal process of the arytenoid cartilages anteriorly. The thyroarytenoid muscles pull the arytenoid cartilages anteriorly, thereby slackening the vocal ligaments. The vocalis muscles produce minute adjustments of the vocal ligaments (e.g., as occurs during whispering). They also relax parts of the vocal folds during phonation and singing.

The laryngeal nerves are derived from the vagus nerve (CN X) through the superior laryngeal nerve and the RLN. All intrinsic muscles, except cricothyroid, are innervated by the RLN with fibers from the accessory nerve (CN XI). The external laryngeal nerve supplies the cricothyroid muscle. The supraglottic portion of the laryngeal mucosa is supplied by the internal laryngeal nerve, a branch of the superior laryngeal nerve. The infraglottic portion of the laryngeal mucosa is supplied by the RLN.

Most people (doctors and the general public) do not realize that something can be done to improve a voice that is unsatisfactory or even one that is adequate, but not optimal. Historically, some techniques for voice improvement (e.g., singers, actors, and public speakers have sought out "voice lessons") go back years. However, techniques for voice improvement have expanded and improved recently.

Vocal weakness, breathiness, instability, impaired quality and other characteristics can interfere with social and professional success. Many problems (particularly, breathiness, softness, instability, tremor and change in habitual pitch) are associated commonly with aging. For most people, these vocal characteristics, which lead people to perceive a voice (and its owner) as "old" or "infirm," can be improved or eliminated.

Voice problems that people ascribe to aging, or even to their natural genetic makeup, may be caused or aggravated by medical problems. The possibilities are numerous and include such conditions as reflux, low thyroid function, diabetes, tumors, and many others. It is not surprising that when exercises and medications alone do not provide sufficient improvement, many patients elect voice surgery in an attempt to strengthen their vocal quality and endurance and to improve their quality of life.

Typically, several different procedures have been used to strengthen weak or injured voices. The selection of the operation depends upon the individual persons' vocal condition, physical examination, and consideration of what the person wants. In most cases, surgery is directed toward bringing the vocal folds physically closer together so that they close more firmly. This eliminates the air leak between the vocal folds that occurs as a consequence of vocal aging (atrophy or wasting of vocal muscles or other tissues) or as a result of paresis or paralysis (partial injury to a nerve from a viral infection or other causes). In some cases, the operation is done by injecting a material through the mouth or neck into the tissues adjacent to the vocal fold, to "bulk up" the vocal tissues and bring the vocal folds closer together. This is called injection laryngoplasty and is performed usually using fat, collagen, or hydroxylapatite. Alternatively, the problem can be corrected by performing a thyroplasty. This operation involves making a small incision in the neck. The skeleton of the voice box is entered and the laryngeal tissues are compressed slightly using Gor-Tex or silastic implants.

SUMMARY OF EMBODIMENTS

In accordance with one embodiment of the invention, a method of providing training therapy to a human subject having a weakened voice includes providing an activating switch configured to generate a first signal, generating at least one stimulation parameter, using a processor, in response to receiving the first signal. The stimulation parameter is based on the first signal. The method further includes activating a recurrent laryngeal nerve or vagus nerve in response to receiving the stimulation parameter.

In related embodiments, the activating switch is a sensing electrode configured to detect voice activity and to generate the first signal in response to the detected activity. The sensing electrode may be a microphone that detects acoustic signals related to voice production, may be an impedance sensor that detects changes of impedances related to voice production, and/or may be a pressure sensor that detects changes in pressure related to voice production. The sensing electrode may be configured to detect movement related to voice production. The method may further include determining when the voice activity has reached a predetermined level, and then having the sensing electrode generate the first signal when the predetermined level is reached. The activating switch may be a motion sensor that detects movement of the subject and generates the first signal in response to the detected movement. The activating switch may provide an automated activation based on detecting electromyographic (EMG) activity of a vocalizing muscle. The activating switch may be a manual activator operable by the subject. The activating may include providing a current pulse having a duration of about 0.01 msec to 20 msec and a magnitude in the range of about 0.05 mA to 20 mA. The stimulation parameter may include a stimulation frequency that is approximately reciprocal to a contraction time of a vocal cord adductor of the subject and may include a stimulation frequency that is above a reciprocal of a contraction time of a vocal cord abductor of the subject. The stimulation parameter may include a stimulation voltage that is above a threshold for activation of vocal cord abductor or adductor muscles of the subject. Alternatively, the stimulation parameter may include a stimulation voltage that is above a threshold for activation of vocal cord adductor muscles of the subject and below a threshold for activation of vocal cord abductor muscles of the subject. The stimulation parameter may include a stimulation voltage that is above a threshold for activation of vocal cord abductor muscles of the subject and above a threshold for activation of vocal cord adductor muscles of the subject. The stimulation parameter may include a stimulation voltage so that a net force for activation of adductor muscles is higher than a net force for activation of abductor muscles of the subject.

In accordance with another embodiment of the invention, a stimulation system for training a weakened voice of a human subject includes an activating switch configured to generate a first signal and a processor in communication with the activating switch. The processor has program code for receiving the first signal and for generating at least one stimulation parameter based on the first signal in order to stimulate a recurrent laryngeal nerve or vagus nerve of the subject. The system further includes a stimulating electrode configured to receive the stimulation parameter and to activate the recurrent laryngeal nerve or the vagus nerve of the subject based on the stimulation parameter.

In related embodiments, the stimulating electrode may be a nerve cuff electrode and/or a rod electrode. The stimulation electrode may be configured to provide a range of stimulation voltages. The processor may be configured to detect when the first signal has reached a predetermined level and may be configured to generate the stimulation parameter when the predetermined level is reached.

In accordance with a further related embodiment, the processor may detect when the first signal has reached a predetermined level and respond by generating the simulation parameter. Additionally, the processor may include a pulse generator. In accordance with other related embodiments, the electrodes may be bipolar and/or tripolar. The second signal may be a biphasic current pulse which may have a duration of about 0.001 ms to 50 ms, in most subjects from 0.1 msec to 5 msec, and a magnitude in the range of about 0.05 mA to 20 mA, in most subjects from 0.5 mA to 5 mA.

In accordance with related embodiments, the method may further include providing an energy coupling circuit that inductively couples energy through the skin of the subject. The method may include providing an energy coupling circuit that optically couples energy through the skin of the subject. Stimulating the vocalizing nerve of the subject with an electrical signal may include stimulating the nerve with an electrical signal at a frequency that is approximately reciprocal to the contraction time of the vocal cord adductor of the subject. Stimulating the vocalizing nerve of the subject with an electrical signal may include stimulating the nerve with an electrical signal at a frequency that is above the reciprocal of the contraction time of the vocal cord abductor of the subject.

BRIEF DESCRIPTION OF THE DRAWINGS

The foregoing features of the invention will be more readily understood by reference to the following detailed description, taken with reference to the accompanying drawings, in which:

FIG. 3 is an illustration of a stimulation system for voice lift, in accordance with an embodiment of the invention, and FIG. 3A is an exploded view of the circled region in FIG. 3;

DESCRIPTION OF ILLUSTRATIVE EMBODIMENTS

Figure 1:
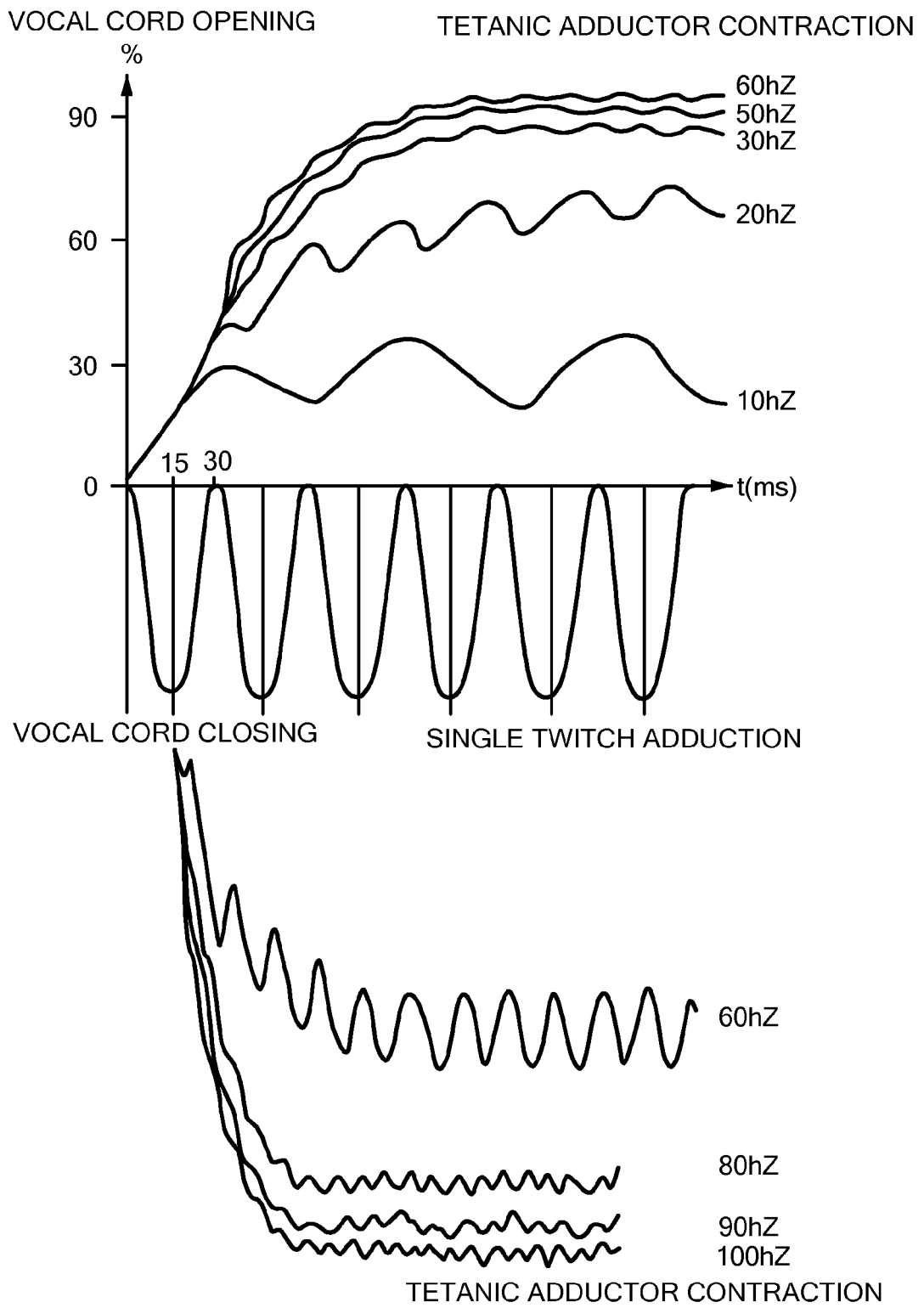
FIG. 1 is a graphical illustration of the underlying principle of frequency-dependent movement of the vocal cords in accordance with an embodiment of the present invention.

A weak voice is typically the consequence of degeneration, weakness of the aging muscle and/or a reduced blood supply. The impairment causes the closing pressure of the vocal folds to be weak. When the closing pressure is weak, the gap between the vocal folds cannot be totally closed/medialized, which leads to a breathy or even worse quality of the voice, an increased risk of aspiration, and a reduced ability for valsalva maneuver (a building up of abdominal pressure by expiration against closed vocal folds).

Alternatively, the vocal cord may not be capable of abduction and/or adduction because of a reduction in the number of re-innervated motor units, (sometimes associated with trophic changes of muscle fibers), disturbance of nerve conductivity, or less maturation of neuromuscular junctions.

Embodiments of the present invention recognize the benefit of training a weakened voice in order to strengthen the muscles of the vocal folds. The training therapy may be accomplished by stimulating the RLN or vagus nerve or by activating the glottic closure reflex by electrical and/or mechanical stimulation in order to selectively activate the abductor muscle, the adductor muscles or both. The advantages of nerve stimulation or reflex activation over intramuscular stimulation are less interference of the stimulation electrode from movement of the muscle, the placement of the implanted electrode is distant from the risky, delicate location of nerve muscle endplates, less invasive surgery is required for implanting the stimulation electrode, etc.

The benefits of using embodiments of the present invention allow the opening and closing of the vocal folds to be activated by the same stimulation electrode based on the stimulation parameters selected due to the differences between the abductor (the opener) and the adductor (the closer) muscles (e.g., frequency-dependent, different thresholds or difference of net forces of adductor and abductor muscles). Exploiting these differences allows for a stimulation system that provides for the selective activation of vocal fold closing muscles, without activation of vocal fold opening muscles, the selective activation of vocal fold opening muscles, without activation of vocal fold closing muscles, and/or the tensioning of vocal folds by graded balanced activation of both opening and closing muscles.

Embodiments of the present invention are directed to a system and method of training or exercising the vocalizing muscles by stimulation of the RLN or vagus nerve innervating the vocalizing muscle, e.g., without the electrical stimulation of the muscle fibers directly. This would allow the surgeon to choose the optimum accessibility to the nerve. In contrast, U.S. Pat. No. 5,111,814 by Goldfarb teaches sensing of electrical activity of normally functioning muscle tissue and stimulating of reinnervated muscle tissue of the larynx.

Embodiments of the present invention are also directed to a system and method of training or exercising the vocalizing muscles by activating the glottic closure reflex, which in turn stimulates the RLN or vagus nerve innervating the vocalizing muscles. This reflex may be activated by stimulation of a nerve, such as the superior laryngeal nerve, the internal or external superior nerve, and/or the glossopharyngeal nerve. It may also be elicited by stimulating mechanoreceptors and/or mucosa of the larynx and/or pharynx, or by the slap reflex. Stimulation may occur by electric currents and/or by mechanical movement or vibration. This variety of stimulation sites may allow a surgeon to choose the optimum treatment for the patient. In some embodiments, stimulation of the RLN or vagus nerve and activation of the glottic closure reflex may be done at the same time.

In some embodiments, the system and method includes an activating switch that activates the stimulation/training system. The activating switch may automatically activate the stimulating system based on various sensed parameters or may manually activate the system, e.g., through the use of a manual activator, operable by the subject. For example, the activating switch may be a sensing electrode configured to sense the voice activity of a vocalizing muscle contraction in the larynx and/or pharynx and stimulating the RLN or vagus nerve innervating the vocalizing muscle, or configured to activate the glottic closure reflex, based on the sensed activity. In this case, the glottis is closed by active electrical sensing/stimulation or electrical sensing and electrical/mechanical stimulation in order to increase the quality of the voice. In contrast, U.S. Pat. No. 5,111,814, incorporated by reference herein, is employed to stimulate muscles which open the glottis in order to increase the amount of inspired air. Similarly, US Patent Publication No. 2006/282127 by Zealear, incorporated by reference herein, is employed to open the vocal folds for the same reason. Thus, embodiments of the present method and device are directed to the sensing activity of vocalizing muscle contraction and not respiratory muscle contraction as, e.g., in US Patent Publication No. 2006/282127 by Zealear.

In some embodiments, the activating switch (e.g., an automatically activated switch or a manual activator) may be used to activate the stimulating system and generate the first signal. For example, the activating switch may be a sensing electrode that automatically senses a vocalizing muscle contraction and then automatically generates the first signal. The training system activates the RLN, vagus nerve, or glottic closure reflex, e.g., by causing stimulation parameters to be sent to the appropriate locations via the stimulation electrode(s). The activating switch allows the stimulation system to be inactive during periods in which vocalization training or exercising would not be needed, e.g., during sleep or while eating, but allows it to be manually or automatically activated when vocalization training or exercising is desired.

After automatically or manually activating the stimulation system using the activating switch, various stimulation parameters may be used in order to take advantage of the differences between the abductor (the opener) and the adductor (the closer) muscles in terms of the threshold voltage for activation, the contraction time, and the number of fibers. Thus, the stimulation parameters include varying amplitude, frequency and/or threshold. For example, the applied voltage and the stimulation frequency may be chosen such that the desired muscles are activated in order to exercise and strengthen them. In general, the stimulation voltage should be directly proportional to the threshold values and the stimulation frequency indirectly proportional to the contraction times.

Embodiments of the present invention may use the frequency-dependent movement of the vocal cords, as shown in FIG. 1. Such movement occurs as a result of the difference in contraction times between the abductor and adductor muscles. The contraction time of the only existing abductor of the vocal cords, the posterior cricoarytenoid (PCA) muscle, is significantly longer than that of the adductor muscles. The RLN contains the nerve fibers to all muscles that act on the vocal cords (except the cricothyroid (CT) muscle which is innervated by the superior laryngeal nerve (SLN)), randomly distributed over the whole nerve. Consequently, an action potential generated by an electrical stimulation always reaches both abductor and adductor muscles. Thus, the glottis first closes due to the faster adductors, then it opens, and ends with relaxation which leads to a vibration of the vocal cords.

When stimulated at a frequency approximately reciprocal to the contraction time of the vocal cord abductor, the action potentials arrive at the muscles at a time when the adductor muscles will have just relaxed from the last activation when the next pulse arrives (as shown below the zero-line on the graph). The abductor, in contrast, has just reached its maximal contraction when the incoming initiation for the next contraction causes their temporal summation (shown above the zero-line). Consequently, resulting tetanic abductor tension overcomes the weaker single twitch adduction.

For stimulation at a frequency approximately reciprocal to the contraction time of the vocal cord adductor, the adductor muscles also reach tetanic contraction, and due to their greater number (4:1) the vocal cords are closed.

Embodiments of the present invention may use the different thresholds for selective activation of the nerves innervating the abductor and adductor muscles. The threshold for activation for abduction is higher than the threshold for adduction because the contraction time of the PCA muscle is significantly longer than that of the adductor muscles. Therefore, the PCA muscle is innervated by nerve fibers of smaller mean nerve fiber diameter which have a threshold for electrical activation higher than for nerve fibers of higher mean nerve fiber diameter, such as innervating the adductor muscles.

When stimulated by a stimulation voltage above the threshold for activation of the nerve fibers innervating the adductor muscle but below the threshold for activation of the nerve fibers innervating the abductor muscle, the abductor muscle fibers will not be activated and therefore relaxed. In contrast, nerve fibers innervating the adductor muscle fibers will be activated, leading to a contraction of the adductor muscles, and the vocal cords will close. When the stimulation voltage is above the respective thresholds for activation for both abductor and adductor muscles, then both sets of muscles will be stimulated. The larger the stimulation amplitude (i.e., the injected amount of charge), the stronger both the abductor and adductor muscles are activated independent of the chosen stimulation frequency, provided the stimulation voltage is above each respective threshold.

Embodiments of the present invention may use the difference of net forces of adductor and abductor muscles due to electrical activation for the nerves innervating the abductor and adductor muscles. The net force for activation of adductor muscles is higher than the net force for activation of abductor muscles due to their greater number (4 adductor muscles versus 1 abductor muscle per side).

When stimulated by a stimulation voltage above the threshold for activation of the nerve fibers innervating the adductor muscles and above the threshold for activation of the nerve fibers innervating the abductor muscle, the abductory (vocal fold opening) net force of the abductor muscle fibers will be lower than the adductory (vocal fold closing) net force of the adductor muscle fibers, as a sum of forces leading to a closing of the vocal folds.

Thus, the stimulation parameters should be selected based on the desired application and selective activation. In summary, when the stimulation voltage is below the threshold value for activation of the adductors, then no stimulation occurs regardless of the stimulation frequency or amplitude used. When the stimulation voltage is above the threshold value for activation of the adductors, but below the threshold value for activation of the abductors, then the vocal folds are closed, regardless of the stimulation frequency or amplitude used, which should benefit patients having a weakened voice in need of exercising the muscles. When the stimulation voltage is above the threshold value for activation of the abductors (and thus above the threshold value for activation of the adductors as well), then the vocal folds may be opened due to tetanic contraction of the abductor muscle when the stimulation frequency is approximately the stimulation frequency of the abductor muscle and the amplitude is low. However, the vocal folds may be opening when these same conditions are applied (the stimulation voltage is above the threshold value for activation of the abductors and the stimulation frequency is approximately the stimulation frequency of the abductor muscle) but a high amplitude is used such that the force of tetanically contracted abductor muscle is greater than the twitch contractions of the adductor muscles, which should benefit patients having a weakened voice in need of exercising the muscles. If an even higher amplitude is used such that the force of tetanically contracted abductor muscle is less than the twitch contractions of the adductor muscles, then the vocal folds may be closing (although there may be a ripple or vibration depending on the stimulation frequency) because the higher applied amplitude overrules tetanic contraction of the abductor muscle. When the stimulation voltage is above the threshold value for activation of the abductors and the stimulation frequency is approximately the stimulation frequency of the adductor muscle, then the vocal folds are closed, regardless of the amplitude used, which should benefit patients having a weakened voice in need of exercising the muscles. For example, depending on the stimulation parameters, a low amplitude may be less than approximately 1.5 mA, a high amplitude may be about 1 to 3 mA, and a very high amplitude may be greater than about 2.5 mA for a pulse duration of about 0.5 ms.

Consequently, based on the stimulation parameters used (such as described above, as well as other combinations), there may be various switching scenarios for the adductor and abductor muscles that are beneficial to selectively activate the vocalizing muscles in order to exercise or train the muscles. For example, with the selection of a stimulation frequency approximately equal to the stimulation frequency of the abductor muscle, a low amplitude, and a stimulation voltage greater than the stimulation voltage for the adductor muscles, the stimulation voltage may be switched between a voltage less than the stimulation voltage of the abductor muscle to a stimulation voltage greater than the stimulation voltage of the abductor muscle, which causes the vocal cords to switch between a closed and an open state. Similarly, with the selection of a stimulation frequency approximately equal to the stimulation frequency of the abductor muscle and the stimulation voltage to greater than the stimulation voltage for the abductor muscles, the amplitude may be switched between a low value and a high value (or very high value), which causes the vocal cords to switch between an opened and an opening (or closing) state. Likewise, with the selection of a stimulation frequency approximately equal to the stimulation frequency of the abductor muscle and a low amplitude, the stimulation frequency may be switched between the stimulation frequency of the abductor muscle and the adductor muscles, which causes the vocal cords to switch between an opened and a closed state.

Embodiments of the present invention include stimulation electrode(s) that are configured to provide various stimulation voltages, frequencies and/or amplitudes, so that the various stimulation parameters may be implemented.

In embodiments of the present invention, the RLN or vagus nerve is stimulated directly or indirectly (via the glottic closure reflex), and the muscle is not simulated directly, because more than 10 times less power is necessary for activation of a nerve than of the muscle itself. Additionally, a nerve-cuff-electrode can be positioned along the nerve far from moving muscles and tissue and far from sensitive receptors, which would produce unwanted reactions.

Figure 2:
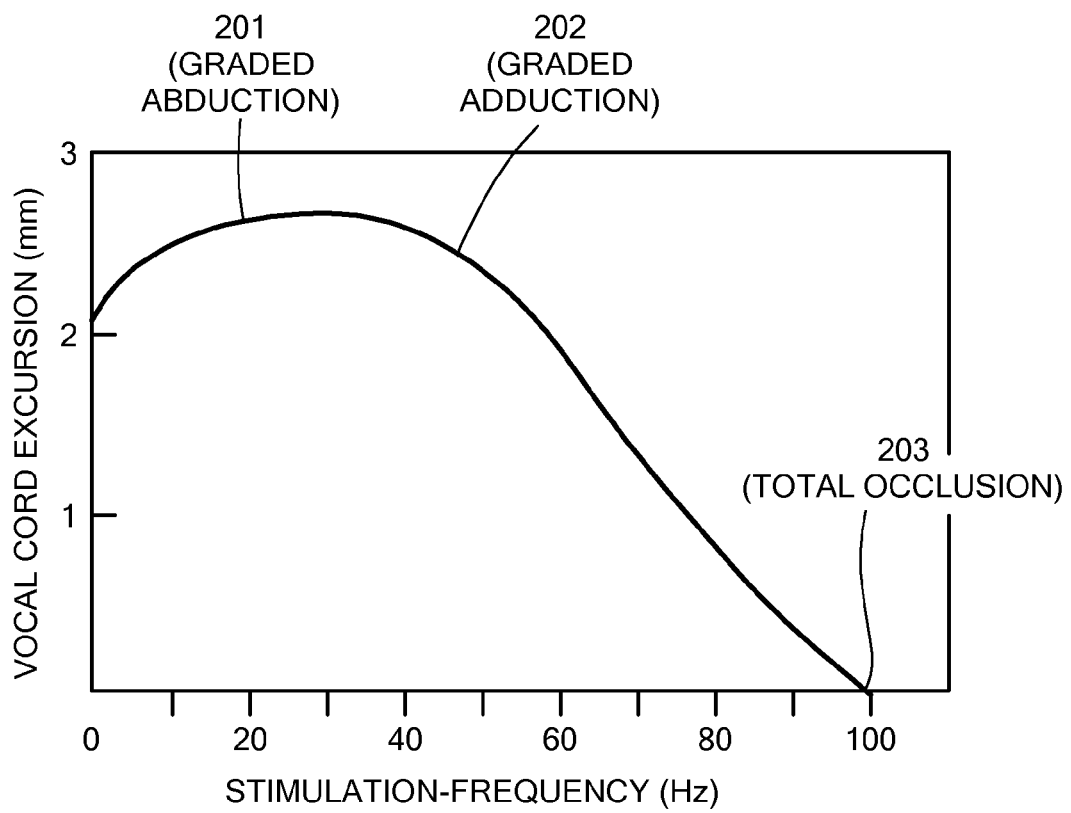
FIG. 2 is a graphical illustration of the frequency-dependent motion of the vocal cords in accordance with the embodiment of FIG. 1.

FIG. 2 is a graphical illustration of the frequency-dependent motion of the vocal cords. Stimulation at 10 to 30 Hz causes a graded abduction 201 of the vocal cords. Above 30 Hz graded cord adduction occurs 202, with total airway occlusion 203 at 100 Hz by bilateral stimulation.

FIGS. 3 and 3A are illustrations of a stimulation system that may be used to produce the training therapy according to one embodiment of the present invention. The stimulation system for voice lift includes one or more stimulating (efferent) electrodes 301 and an activating switch (not shown) that is configured to generate a first signal. The activating switch (e.g., an automatically activated switch or a manual activator) may be used to turn on the training system and generate the first signal. For example, the activating switch may be one or more sensing (afferent) electrodes (not visible) that automatically senses a vocalizing muscle contraction and then automatically generates the first signal or may be a manual activator that is activated by the user, e.g., a switch or toggle. The stimulation system also includes a processor 303, which may include a pulse generator. The processor 303 may be implanted in the patient's chest, and the stimulating electrodes 301 may be wrapped around or placed near or in contact with the vagus nerve or RLN 302 along with the electrode leads 304 and safety loops 305. Alternatively, the stimulation electrodes 301 may be used indirectly to stimulate the RLN or vagus nerve by activating the glottic closure reflex, by stimulation of a nerve, such as the superior laryngeal nerve, the internal or external superior nerve, and/or the glossopharyngeal nerve. The stimulation electrodes 301 may be used to stimulate the glottic closure reflex by stimulating mechanoreceptors and/or mucosa of the larynx and/or pharynx, or by the slap reflex. As mentioned above, the stimulation may be electrical and/or mechanical or vibratory stimulation.

Embodiments of the present system may be totally or partially implanted in a human subject. For example, the stimulator may include a housing that can be very small with all of the implant's electronic components contained in a robust and compact hermetically sealed case. Energy and necessary information may be inductively or optically transferred through the skin of the subject. This can be achieved by either enclosing the electronic circuitry inside a metallic case with a secondary coil placed aside or around the case. Similarly, this may be achieved by enclosing the electric circuitry and a secondary coil inside a dielectric case.

Figure 4:
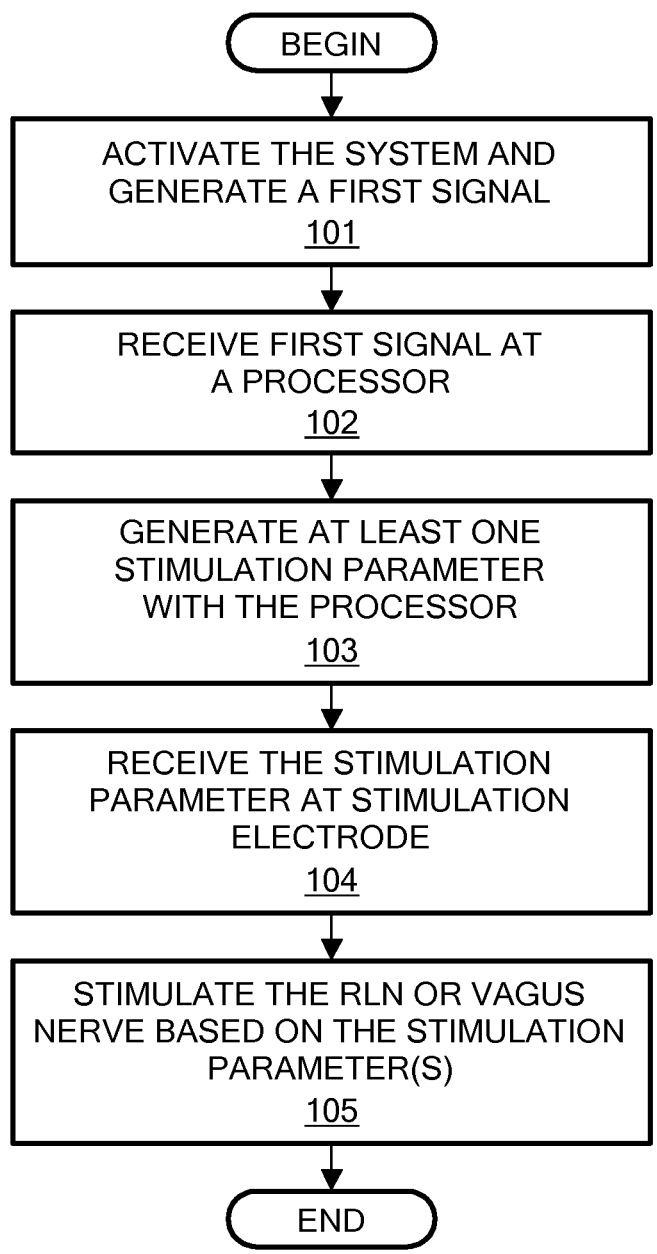
FIG. 4 is a flow chart illustrating a method for stimulating a vocalizing nerve in a human subject having a weak voice in accordance with an embodiment of the invention.

Referring also to FIG. 4, the system may be activated by an activating switch (step 101). The activating switch may activate the system by automatically sensing parameters related to the subject. For example, the system may be automatically activated using a sensing (afferent) part of a closed loop system that includes one or more sensing electrodes that detect various parameters of the subject, e.g., the voice activities of the infrahyoidal muscles or signals recorded by the alternative sensors. For example, the sensing electrode(s) may be configured to detect electromyographic (EMG) activity of a vocalizing muscle and/or to detect movement related to voice production. The sensing electrode may be a microphone that detects acoustic signals related to voice production, an impedance sensor that detects changes of impedances related to voice production, and/or a pressure sensor that detects changes in pressure related to voice production. The activating switch may manually activate the system by a manual activator that is operable by the subject. The activating switch may generate a first signal in response to the activity that has been automatically detected or may generate a first signal in response to the manual activator.

The first signal is received (step 102) at a processor 303. The processor 303 may include a pulse generator. The processor 303 receives the first signal from the activating switch and generates at least one stimulation parameter (step 103) that is based on the first signal. The stimulation parameter or second signal may be a biphase current pulse, and the biphase current pulse may have a duration of about 0.001 ms to 50 ms, in most subjects from about 0.1 msec to 5 msec, and a magnitude in the range of about 0.05 mA to 20 mA, in most subjects from about 0.5 mA to 5 mA.

The stimulation parameter from the processor 303 is received by one or more stimulating electrodes 301 (step 104), and the stimulating electrode(s) 301 stimulate a vocalizing nerve, such as the RLN or the vagus nerve directly (from which the RLN originates and which is easier to handle surgically) (step 105), in accordance with the stimulation parameter. Alternatively, the stimulating electrode(s) 301 may stimulate the RLN or the vagus nerve indirectly by activating the glottic closure reflex(es), which then activate the RLN or vagus nerve. In accordance with an embodiment of the invention, the stimulation is limited to the time periods of voice production or swallowing or valsalva maneuver.

The stimulating electrodes and the optional sensing electrodes may be either bipolar or tripolar. Similarly, one electrode may be bipolar and one electrode may be tripolar. The electrode leads 304 should be sufficiently damage-resistant. The lead body should be arranged in a way, so that the nerve and the stimulator are influenced as little as possible by movements of the muscles, the neck and the head.

Embodiments can be used to activate the vocal cord adduction in patients with a weakened voice by stimulating the whole innervating RLN or alternatively, the vagus nerve, from which the RLN originates.

Figure 5:
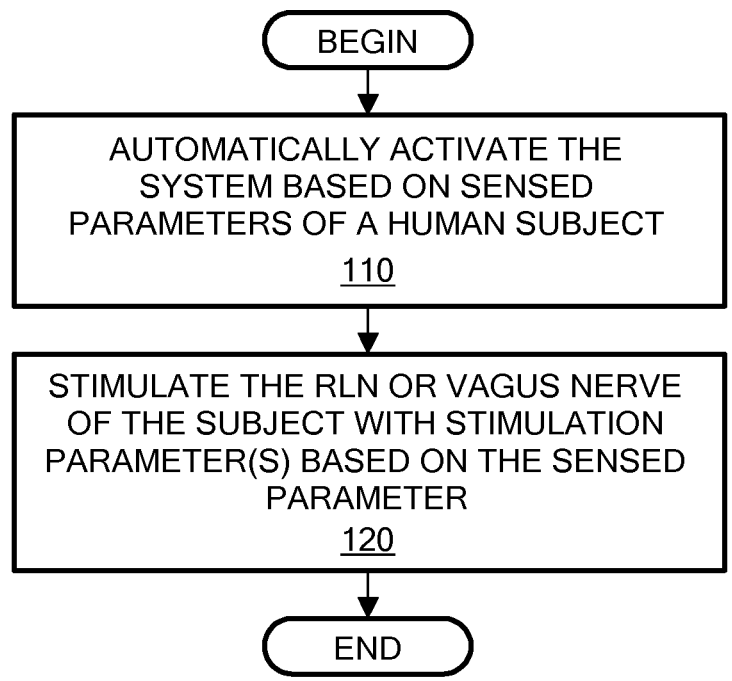
FIG. 5 is a flow chart illustrating a method of training the weak voice of a human subject using an automatically activated system in accordance with an embodiment of the invention.

FIG. 5 is a flow chart illustrating a method of training therapy of a human subject in accordance with one embodiment of the invention. An activating switch automatically activates the training system based on sensed parameters of the subject and generates a first signal (step 110). For example, the activating switch sense an electrical activity of a vocalizing muscle (such as the infrahyoidal muscles) of a human subject using one or more sensing electrodes. A vocalizing nerve (such as the RLN or the vagus nerve) of the subject is directly stimulated with an electrical signal based on the generated first signal (step 120). Alternatively, the RLN or vagus nerve may be indirectly stimulated by the activation of the glottic closure reflex(es) based on the generated first signal. The stimulation/activation parameters may include stimulating the RLN or vagus nerve with an electrical signal at a stimulation frequency above the reciprocal value of the contraction time of the vocal cord adductor of the subject. Stimulating the vocalizing nerve of the subject with an electrical signal may include stimulating the nerve with an electrical signal at a frequency approximately reciprocal to the contraction time of the vocal cord adductor of the subject and above the reciprocal of the contraction time of the vocal cord abductor of the subject.

Figure 6:
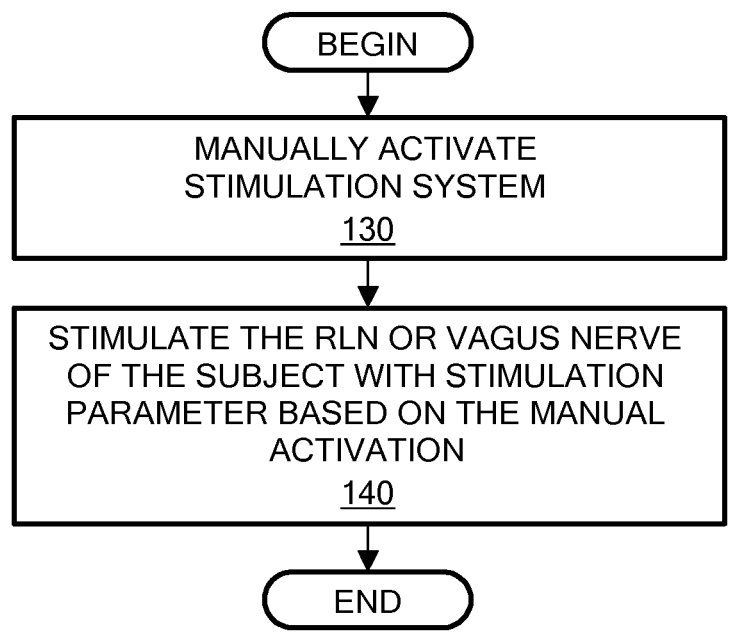
FIG. 6 is a flow chart illustrating a method of training the weak voice of a human subject using a manual activation in accordance with an embodiment of the invention.

FIG. 6 is a flow chart illustrating a method of training therapy of a human subject using a manual activation of the system in accordance with one embodiment of the invention. The stimulation system is manually activated in step 130 by a manual activator used by the subject. The manual activator may send a first signal to the processor 303, which may include a pulse generator. The processor 303 receives the first signal from the activating switch and generates at least one stimulation parameter that is based on the first signal. The RLN or vagus nerve is then activated (step 140) based on the stimulation parameter. Alternatively, the RLN or vagus nerve may be indirectly activated, via the glottic closure reflex, based on the stimulation parameter. The stimulation may be electrical and/or mechanical or vibratory stimulation.

Some embodiments of the processor 303 may be implemented as hardware, software (e.g., a computer program product), or a combination of both software and hardware. For example, embodiments may be implemented as a computer program product for use with a computer system. Such implementation may include a series of computer instructions or program code fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

While the invention has been described in connection with specific embodiments thereof, it will be understood that it is capable of further modification. This application is intended to cover any variation, uses, or adaptions of the invention and including such departures from the present disclosure as come within known or customary practice in the art to which the invention pertains.

What is claimed is:

1. A method of providing training therapy to a human subject having a weakened voice, the method comprising:
   providing an activating switch configured to generate a first signal;
   generating at least one stimulation parameter, using a processor, in response to receiving the first signal, the stimulation parameter being based on the first signal and including a stimulation voltage that is above a threshold for activation of vocal cord adductor muscles of the subject and below a threshold for activation of vocal cord abductor muscles of the subject; and
   activating a recurrent laryngeal nerve or vagus nerve in response to receiving the stimulation parameter.

2. A method according to claim 1, wherein the activating switch is a sensing electrode configured to detect voice activity and to generate the first signal in response to the detected activity.

3. A method according to claim 2, wherein the sensing electrode is a microphone that detects acoustic signals related to voice production.

4. A method according to claim 2, wherein the sensing electrode is an impedance sensor that detects changes of impedances related to voice production.

5. A method according to claim 2, wherein the sensing electrode is a pressure sensor that detects changes in pressure related to voice production.

6. A method according to claim 2, wherein the sensing electrode is configured to detect movement related to voice production.

7. A method according to claim 2, further comprising:
   determining when the voice activity has reached a predetermined level, wherein the sensing electrode responds by generating the first signal when the predetermined level is reached.

8. A method according to claim 1, wherein the activating switch is a motion sensor that detects movement of the subject and generates the first signal in response to the detected movement.

9. A method according to claim 1, wherein the activating switch provides an automated activation based on detecting electromyographic (EMG) activity of a vocalizing muscle.

10. A method according to claim 1, wherein the activating switch is a manual activator operable by the subject.

11. A method according to claim 1, wherein the activating includes providing a current pulse having a duration of about 0.01 msec to 20 msec and a magnitude in the range of about 0.05 mA to 20 mA.

12. A method according to claim 1, wherein the stimulation parameter includes a stimulation frequency that is approximately reciprocal to a contraction time of a vocal cord adductor of the subject.

13. A method according to claim 1, wherein the stimulation parameter includes a stimulation frequency that is above a reciprocal of a contraction time of a vocal cord abductor of the subject.

14. A method according to claim 1, further comprising
   varying the stimulation parameters in order to selectively activate the abductor muscle, the adductor muscles or both, including varying the stimulation voltage to above a threshold for activation of vocal cord abductor muscles of the subject.

15. A method according to claim 1, further comprising varying the stimulation parameters in order to selectively activate the abductor muscle, the adductor muscles or both, wherein the stimulation parameters include the stimulation voltage, stimulation frequency and/or amplitude.

16. A method according to claim 15, wherein varying the stimulation parameters include varying the stimulation voltage to above a threshold for activation of vocal cord abductor muscles of the subject and above a threshold for activation of vocal cord adductor muscles of the subject.

17. A method according to claim 15, wherein varying the stimulation parameters include varying the stimulation voltage so that a net force for activation of adductor muscles is higher than a net force for activation of abductor muscles of the subject.

18. A stimulation system for training a weakened voice of a human subject, the system comprising:
   an activating switch configured to generate a first signal;
   a processor in communication with the activating switch, the processor having program code for receiving the first signal and for generating at least one stimulation parameter based on the first signal, the at least one stimulation parameter including a stimulation voltage that is above a threshold for activation of vocal cord adductor muscles of the subject and below a threshold for activation of vocal cord abductor muscles of the subject in order to stimulate a recurrent laryngeal nerve or vagus nerve of the subject; and
   a stimulating electrode configured to receive the stimulation parameter and to activate the recurrent laryngeal nerve or the vagus nerve of the subject based on the stimulation parameter.

19. A system according to claim 18, wherein the stimulating electrode is a nerve cuff electrode, a rod electrode or combinations thereof.

20. A system according to claim 18, wherein the stimulation electrode is configured to provide a range of stimulation voltages.

21. A system according to claim 18, wherein the processor is configured to detect when the first signal has reached a predetermined level and configured to generate the stimulation parameter when the predetermined level is reached.

* * * * *